(12) United States Patent
Rubröder et al.

(10) Patent No.: US 6,380,355 B1
(45) Date of Patent: *Apr. 30, 2002

(54) PROCESS FOR OBTAINING INSULIN PRECURSORS HAVING CORRECTLY BONDED CYSTINE BRIDGES

(75) Inventors: Franz-Josef Rubröder, Vilmar; Reinhold Keller, Bad Soden, both of (DE)

(73) Assignee: Aventis Pharma Deutschland GmbH, Frankfurt am Main (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/386,303

(22) Filed: Aug. 31, 1999

Related U.S. Application Data

(62) Division of application No. 09/134,836, filed on Aug. 19, 1998, now Pat. No. 5,986,048.

(30) Foreign Application Priority Data

Aug. 18, 1997 (DE) .......................... 197 35 711

(51) Int. Cl.⁷ .......................... A61K 38/00; C07K 5/00; C07K 7/00
(52) U.S. Cl. ........................................ 530/303; 530/324
(58) Field of Search ................................. 530/303, 324

(56) References Cited

U.S. PATENT DOCUMENTS

| 4,801,684 A | 1/1989 | Grau |
| 5,473,049 A | 12/1995 | Obermeier et al. |
| 5,663,291 A | 9/1997 | Obermeier et al. |
| 5,986,048 A | 11/1999 | Rubröder et al. |

FOREIGN PATENT DOCUMENTS

| EP | 0 055 945 A2 | 7/1982 |
| EP | 0 600 372 A1 | 6/1994 |
| EP | 0 668 292 A2 | 8/1995 |
| EP | 0 906 918 A | 4/1999 |
| WO | WO 86/04335 | 7/1986 |
| WO | WO 91/03550 | 3/1991 |
| WO | WO 96/20724 | 7/1996 |

OTHER PUBLICATIONS

Chance, et al. Edo., Peptides: Synthesis, Structure, Function, Pierce Chemical Co., Rockford IL. pp 721–728, 1981.*
Frank et al. Eds., Peptides: Synthesis, Structure, Function, Pierce Chemical Co., Rockford, IL, 1981, pp 729–738.*

* cited by examiner

Primary Examiner—Avis M. Davenport
(74) Attorney, Agent, or Firm—Finnegan, Henderson, Farabow, Garrett and Dunner, L.L.P.

(57) ABSTRACT

The present invention relates to an improved process for obtaining a precursor of an insulin or insulin derivative having correctly bonded cystine bridges in the presence of cysteine or cysteine hydrochloride and chaotropic auxiliary.

17 Claims, No Drawings

PROCESS FOR OBTAINING INSULIN PRECURSORS HAVING CORRECTLY BONDED CYSTINE BRIDGES

This is a division of U.S. patent application Ser. No. 09/134,836, filed on Aug. 19, 1998 now U.S. Pat. No. 5,986,048.

BACKGROUND OF THE INVENTION

The present invention relates to an improved process for obtaining a precursor of insulin or an insulin derivative having correctly bonded cystine bridges in the presence of cysteine or cysteine hydrochloride and a chaotropic auxiliary.

Human insulin is a protein with two amino acid chains together having 51 amino acid residues. Six cysteine residues are found in the two amino acid chains, each two cysteine residues being bonded to one another via a disulfide bridge. In biologically active human insulin, the A and B chains are bonded to one another via two cystine bridges, and a further cystine bridge is found in the A chain. Within a human insulin molecule, looked at statistically, there are 15 possibilities for the formation of disulfide bridges. In biologically active human insulin, only one of the 15 possibilities is found. The following cysteine residues are linked to one another in human insulin:

A 6–A 11
A 7–B 7
A 20–B 19

The letters A and B represent the respective insulin amino acid chain and the numbers represent the position of the amino acid residue, which is counted from the amino to the carboxyl end of the respective amino acid chain. Disulfide bridges can also be formed between two human insulin molecules such that an incalculable number of different disulfide bridges can easily result.

A known process for the preparation of human insulin is based on the use of human proinsulin. Human proinsulin is a protein having a linear amino acid chain of 86 amino acid residues, the A and B chains of the human insulin being bonded to one another via a C peptide having 35 amino acid residues. The formation of the disulfide bridges found in human insulin takes place via an intermediate, the cysteine residues of the human insulin being provided with a sulfur protective group, e.g. an S-sulfonate (—S—SO3—) group (EP 0 037 255). A process for obtaining proinsulin having correctly bonded cystine bridges is additionally known (Biochemistry, 60, (1968), pages 622 to 629), which starts from proinsulin obtained from porcine pancreas, in which the cysteine residues are present as thiol residues (—SH). The term "correctly bonded cystine bridges" is understood as meaning the disulfide bridges which are found in biologically active insulin from mammals.

Recombinant DNA processes allow precursors of insulin or insulin derivatives, in particular human proinsulin or proinsulin which has an amino acid sequence and/or amino acid chain length differing from human insulin, to be prepared in microorganisms. The proinsulins prepared from genetically modified *Escherichia coli* cells do not have any correctly bonded cystine bridges. A process for obtaining human insulin using *E. coli* (EP 0 055 945) is based on the following process steps:

Fermentation of the microorganisms—cell disruption—isolation of the fusion protein—cyanogen halide cleavage of the fusion protein—isolation of the cleavage product having the proinsulin sequence—protection of the cystine residues of proinsulin by S-sulfonate groups—chromatographic purification of the S-sulfonate—formation of the correctly bonded cystine bridges—desalting of the proinsulin—chromatographic purification of the proinsulin having correctly bonded cystine bridges—concentration of the proinsulin solution— chromatographic purification of the concentrated proinsulin solution—enzymatic cleavage of the proinsulin to obtain human insulin—chromatographic purification of the resulting human insulin.

Disadvantages of this process are the number of process steps and the losses in the purification steps, which lead to a low yield of insulin. From the stage of the isolated fusion protein via cyanogen halide cleavage, sulfitolysis and purification of the proinsulin, a loss of up to 40% of the proinsulin product has to be expected (EP 0 055 945). Similarly, high losses can occur in the course of the subsequent required to obtain the final product.

Yield increases in the preparation of human insulin or insulin derivatives by recombinant DNA means can be achieved if the number of process steps necessary can be significantly reduced.

EP 0 600 372 A1 (or U.S. Pat. No. 5,473,049) and EP 0 668 292 A2 disclose an improved process for obtaining insulin or insulin derivatives, in which the insulin precursor or precursor of the insulin derivative whose cystine bridges are not present in correctly linked form is reacted in the presence of a mercaptan, for example cysteine, and of at least one chaotropic auxiliary, for example urea or guanidine hydrochloride, to give an insulin precursor or precursor of the insulin derivative having correctly bonded cystine bridges. In the known process, these proteins are first dissolved in a very low concentration in aqueous solutions of a chaotropic auxiliary or of mixtures of various chaotropic auxiliaries. The protein mixture is then mixed with an aqueous mercaptan solution.

Surprisingly, it has now been found that the yields of correctly folded precursors of insulins or insulin derivatives can be increased and the reaction times for the folding process can be reduced by delaying the dissolution of the precursor in a first step by means of the chaotropic auxiliary. Instead, a mercaptan, such as cysteine or cysteine hydrochloride, is introduced into the aqueous suspension of the precursor in the first step, followed by dissolution of the precursor in a subsequent step by introducing a chaotropic auxiliary, and finally bringing about the correct folding of the precursor by dilution of the mixture to a preferred cysteine or cysteine hydrochloride concentration with an appropriate amount of water.

SUMMARY OF THE INVENTION

Accordingly, the present invention relates to a process for obtaining a precursor of insulin or an insulin derivative having correctly bonded cystine bridges in the presence of cysteine or cysteine hydrochloride and of a chaotropic auxiliary, which comprises successively carrying out the following steps:

(a) mixing an aqueous suspension of the precursor of insulin or an insulin derivative with an amount of cysteine or cysteine hydrochloride which results in approximately 1 to 15 SH residues of the cysteine or cysteine hydrochloride per cysteine residue of the precursor, (b) introducing the cysteine- or cysteine hydrochloride-containing suspension of the precursor into an approximately 4 to 9 molar solution of the chaotropic auxiliary at a pH of approximately 8 to 11.5 and a temperature of approximately 15° C. to 55° C., keeping the mixture obtained at this temperature for approximately 10 to 60 minutes; and (c) introducing the mixture at a pH of approximately 8 to 11.5 and a temperature of approximately 5° C. to 30° C. into an amount of water which results in a dilution of the concentration of the cysteine or of the cysteine hydrochloride in the mixture to approximately 1 to 5 mM and of the chaotropic auxiliary to approximately 0.2 to 1.0 M.

DETAILED DESCRIPTION

Preferably, the process is one wherein in step (a) the amount of cysteine or cysteine hydrochloride corresponds to an amount which results in approximately 1 to 6 SH residues of the cysteine or cysteine hydrochloride per cysteine residue of the precursor, in step (b) the cysteine- or cysteine hydrochloride-containing suspension of the precursor is introduced into an approximately 4 to 9 molar solution of the chaotropic auxiliary at a pH of approximately 8 to 11 and a temperature of approximately 30° C. to 45° C. and the mixture obtained is kept for approximately 20 to 40 minutes at this temperature; and in step (c) the mixture is introduced at a pH of approximately 8 to 11 and at a temperature of approximately 15° C. to 20° C. into an amount of water which results in a dilution of the concentration of the cysteine or of the cysteine hydrochloride in the mixture to approximately 1 to 5 mM and a concentration of the chaotropic auxiliary of approximately 0.2 to 1.0 M.

Chaotropic auxiliaries are compounds which break hydrogen bridges in aqueous solution, for example ammonium sulfate, guanidine hydrochloride, ethylene carbonate, thiocyanate, dimethyl sulfoxide and urea.

In the process of this invention, the chaotropic auxiliary employed is preferably guanidine, guanidine hydrochloride or particularly preferably, urea.

The concentration of the chaotropic auxiliary in step (b) of the process of this invention is preferably 7.0 to 9M, the temperature in step (b) is preferably 40° C. and the pH in step (b) is preferably 10 to 11.

In the process of this invention, the pH in step (c) is preferably 10 to 11. In step (c) of the process of this invention, the amount of water into which the mixture is introduced is preferably selected such that it results in a dilution of the cysteine or cysteine hydrochloride concentration in the mixture to approximately 2.5 to 3 mM and a concentration of the chaotropic auxiliary of approximately 0.5 M.

Particularly preferably, the process according to the invention is one wherein the concentration of the chaotropic auxiliary in step (b) is approximately 8 M, the temperature in step (b) is approximately 40° C., the pH in step (b) is approximately 10.6, the pH in step (c) is approximately 10.6 and in step (c) the amount of water results in a dilution of the concentration of the cysteine or of the cysteine hydrochloride in the mixture to approximately 2.5 to 3 mM and a concentration of the chaotropic auxiliary of approximately 0.5 M.

The result of the process of this invention is a precursor of insulin or an insulin derivative, in particular a proinsulin, whose cystine bridges are correctly bonded.

Insulin derivatives are derivatives of naturally occurring insulins, namely human insulin (see SEQ ID NO:1=A chain of human insulin; see SEQ ID NO:2=B chain of human insulin, sequence listing) or animal insulins, which differ by substitution of at least one naturally occurring amino acid residue and/or addition of at least one amino acid residue and/or organic residue of the corresponding, otherwise identical, naturally occurring insulin.

From the precursor of the insulin or insulin derivative having correctly bonded cystine bridges obtained with the aid of this invention, it is finally possible in combination with the process described in EP 0 600 372 A1 (or U.S. Pat. No. 5,473,049) or in EP 0 668 292 A2, to prepare an insulin or an insulin derivative having correctly bonded cystine bridges by enzymatic cleavage by means of trypsin or a tripsin-like enzyme and, if appropriate, additionally by means of carboxypeptidase B and subsequent purification on an adsorber resin.

The insulin or insulin derivative which can be prepared from the precursor can preferably be described by formula I

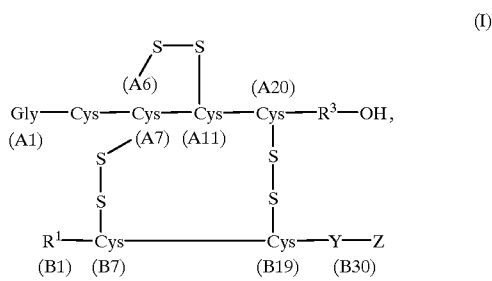

in which

Y is a genetically encodable amino acid residue;

z is a) an amino acid residue from the group consisting of His, Arg and Lys, b) a peptide having 2 or 3 amino acid residues, comprising the amino acid residue Arg or Lys at the carboxyl end of the peptide, c) a peptide having 2–35 genetically encodable amino acids, comprising 1 to 5 histidine residues, or d) OH;

$R^1$ is a phenylalanine residue (Phe) or a covalent bond, $R^3$ is a genetically encodable amino acid residue, and where the radicals A2–A20 of the amino acid sequence of the A chain of human insulin (not shown for the simplification of the formula I) correspond to animal insulin or an insulin derivative and the radicals B2–B29 of the amino acid sequence of the B chain of human insulin (not shown for the simplification of the formula I) correspond to animal insulin or an insulin derivative.

The amino acid sequence of peptides and proteins is indicated from the N-terminal end of the amino acid chain onward. The details in formula I in brackets, e.g. A6, A20, B1, B7 or B19, correspond to the position of amino acid residues in the A or B chains of the insulin.

The term "genetically encodable amino acid residue" represents the amino acids Gly, Ala, Ser, Thr, Val, Leu, Ile, Asp, Asn, Glu, Gln, Cys, Met, Arg, Lys, His, Tyr, Phe, Trp, Pro and selenocysteine.

The terms "residues A2–A20" and "residues B2–B29" of "animal insulin" are understood as meaning, for example, the amino acid sequences of insulin from cattle, pigs or chickens. The terms "residues A2–A20" and "B2–B29" of insulin derivatives represent the corresponding amino acid sequences of human insulin which are formed by the replacement of amino acids by other genetically encodable amino acids.

The A chain of human insulin has the following sequence (SEQ ID NO:1):
Gly Ile Val Glu Gln Cys Cys Thr Ser Ile Cys Ser Leu Tyr Gln Leu Glu Asn Tyr Cys Asn.

The B chain of human insulin has the following sequence (SEQ ID NO:2):
Phe Val Asn Gln His Leu Cys Gly Ser His Leu Val Glu Ala Leu Tyr Leu Val Cys Gly Glu Arg Gly Phe Phe Tyr Thr Pro Lys Thr.

In human insulin, $R^3$ in formula I is asparagine (Asn), $R^1$ is phenylalanine (Phe), Y is threonine (Thr) and Z is OH.

The process according to the present invention is particularly suitable for obtaining a precursor of insulin or an insulin derivative having the formula II, whose cystine bridges (not shown in formula II) are correctly folded, $$R^2-R^1-(B2-B29)-Y-X-Gly-(A2-A20)-R^3 \qquad (II),$$

in which
$R^2$ is
  a) a hydrogen atom,
  b) an amino acid residue from the group consisting of lysine (Lys) and arginine (Arg), or
  c) a peptide having 2 to 45 amino acid residues, comprising the amino acid residue lysine (Lys) or arginine (Arg) at the carboxyl end of the peptide;
$R^1$ is a phenylalanine residue (Phe) or a covalent bond;
(B2–B29) are the amino acid residues in the positions B2 to B29 of the B chain of human insulin, animal insulin or an insulin derivative which is optionally varied in one or more of these positions;
Y is a genetically encodable amino acid residue;
X is
  a) an amino acid residue from the group consisting of lysine (Lys) and arginine (Arg),
  b) a peptide having 2 to 35 amino acid residues, comprising the amino acid residue lysine (Lys) or arginine (Arg) at the N-terminal end and at the carboxyl end of the peptide, or
  c) a peptide having 2 to 35 genetically encodable amino acids, comprising 1 to 5 histidine residues;
(A2–A20) are the amino acid residues in the positions A2 to A20 of the A chain of human insulin, animal insulin or an insulin derivative which is optionally varied in one or more of these positions; and
$R^3$ is a genetically encodable amino acid residue.

1. In a first preferred embodiment, in formula II:
$R^2$ is
  a) a hydrogen atom, or
  b) a peptide having 2 to 25 amino acid residues, comprising the amino acid residue arginine (Arg) at the carboxyl end of the peptide;
$R^1$ is a phenylalanine residue (Phe);
(B2–B29) are the amino acid residues in the positions B2 to B29 of the B chain of human insulin;
Y is an amino acid residue from the group consisting of alanine (Ala), threonine (Thr) and serine (Ser);
X is the amino acid residue arginine (Arg) or a peptide having the amino acid sequence of the C chain of human insulin;
(A2–A20) are the amino acid residues in the positions A2 to A20 of the A chain of human insulin; and $R^3$ is an amino acid residue from the group consisting of asparagine (Asn), serine (Ser) and glycine (Gly)

The C chain of human insulin has the following sequence (SEQ ID NO:3):

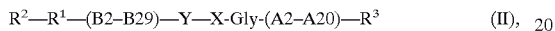

Arg Arg Glu Ala Glu Asp Leu Gln Val Gly Gln Val

Glu Leu Gly Gly Gly Pro Gly Ala Gly Ser Leu Gln

Pro Leu Ala Leu Glu Gly Ser Leu Gln Lys Arg.

2. In a second preferred embodiment, in formula II:
$R^2$ is
  a) a hydrogen atom, or
  b) a peptide having 2 to 15 amino acid residues, at whose carboxyl end is found an arginine residue (Arg);
$R^1$ is a phenylalanine residue (Phe);
(B2–B29) are the amino acid residues in the positions B2 to B29 of the B chain of human insulin;
Y is a threonine residue (Thr);
X is the amino acid residue arginine (Arg) or a peptide having 2 to 35 amino acid residues, where at the beginning and at the end of the peptide there are two basic amino acid residues, in particular arginine (Arg) and/or lysine (Lys);
(A2–A20) are the amino acid residues in the positions A2 to A20 of the A chain of human insulin; and
$R^3$ is the amino acid residue asparagine (Asn) or glycine (Gly).

The residue Z of the insulin or of the insulin derivative of the formula I is, as a rule, part of the amino acid sequence of X of the precursor of the formula II and results from the activity of the proteases such as trypsin, trypsin-like enzyme or carboxypeptidase B, therefor The radical $R^3$ is the amino acid residue which is in position A21 of the A chain of insulin. The radical Y is the amino acid residue which is in position B30 of the B chain of insulin.

Trypsin or trypsin-like enzymes are proteases which cleave amino acid chains at the arginine or lysine residue. Carboxypeptidase B is an xoprotease which removes basic amino acid residues such as Arg or Lys which are at the carboxy-terminal end of amino acid chains. (Kemmler et al., J. Biol. Chem. 246, pages 6786–6791).

From the precursor described above as the first preferred embodiment, it is possible, for example, to obtain an insulin or insulin derivative of the formula I having correctly linked cystine bridges, where Y, $R^1$, $R^2$, $R^3$, A2–A20 and B2–B29 have the precursor described above as a first preferred embodiment, and Z is an argine residue (Arg), a peptide residue Arg-Arg or —OH.

From the precursor precursor described above as the second preferred embodiment, it is possible, for example, to obtain an insulin or insulin derivative of the formula I having correctly linked cystine bridges, where Y, $R^1$, $R^2$, $R^3$, A2–A20 and B2–B29 have the meaning precursor described above as a second preferred embodiment, and Z is an arginine residue (Arg), a peptide residue Arg-Arg or Lys-Lys or —OH.

The precursor of the formula II can be formed in microorganisms with the aid of a large number of genetic constructs (EP 0 489 780, EP 0 347 781, EP 0 453 969). The genetic constructs are expressed in microorganisms such as *Escherichia coli* or Streptomycetes during fermentation. The proteins formed are deposited in the interior of the microorganisms (EP 0 489 780) or secreted into the fermentation solution.

For the process according to the invention, precursors of insulins or of insulin derivatives of the formula II can be employed that are still contaminated with a large number of proteins which originate from the fermentation solution and from the microorganisms directly after the cell disruption. The precursors of the formula II, however, can also be employed in prepurified form, for example after precipitation or chromatographic purification.

EXAMPLE 1

Comparison Example, Prior Art

By fermentation of genetically modified *Escherichia coli* cells (EP 0 489 780), a fusion protein having the following amino acid sequence is prepared.

Proinsulin sequence 1 (SEQ ID NO:4):

```
Ala Thr Thr Ser Thr Gly Asn Ser Ala Arg Phe Val
Asn Gln His Leu Cys Gly Ser His Leu Val Glu Ala
Leu Tyr Leu Val Cys Gly Glu Arg Gly Phe Phe Tyr
Thr Pro Lys Thr Arg Arg Glu Ala Glu Asp Leu Gln
Val Gly Gln Val Glu Leu Gly Gly Gly Pro Gly Ala
Gly Ser Leu Gln Pro Leu Ala Leu Glu Gly Ser Leu
Gln Lys Arg Gly Ile Val Glu Gln Cys Cys Thr Ser
Ile Cys Ser Leu Tyr Gln Leu Glu Asn Tyr Cys Asn
```

Proinsulin sequence 1 corresponds to the formula II, in this formula

X is C-peptide from human insulin (SEQ ID NO:3);
Y is Thr (B30);
$R^1$ is Phe(B1);
$R^2$ is a peptide having 10 amino acid residues;
$R^3$ is Asn (A21); and
A2–A20 is the amino acid sequence of the A chain of human insulin (amino acid residues 2 to 20) and B2–B29 is the amino acid sequence of the B chain of human insulin (amino acid residues 2 to 29).

The expressed fusion protein having the proinsulin sequence 1 collects in the *E. coli* cells and forms inclusion bodies. After completion of the fermentation, the cells are separated off by centrifugation and disrupted by customary high-pressure homogenization. The fusion protein inclusion bodies released are isolated by centrifugation.

20 kg of the isolated fusion protein inclusion bodies (based on dry matter after freeze drying; the proportion of the insulin-containing fusion protein is determined with the aid of HPLC—it is 50%) having the proinsulin sequence 1 are dissolved in 550 liters of an 8 M urea solution at pH 10.6. If appropriate, after centrifugation of small amounts of substances causing turbidity, the clear solution is stirred into 9000 liters of an aqueous cysteine solution (5 kg of cysteine hydrochloride hydrate) at a pH of 10.6 and a temperature of 4° C.

After completion of the folding reaction after about 24 h, the content of proinsulin sequence 1 having correctly bonded cystine bridges in the reaction batch is determined with the aid of analytical HPLC as 3.0 kg, corresponding to a conversion of 30%.

The 9500 liters of solution is adjusted to a pH of 5.0 using 1N HCl and separated. A pH of 9 is then set by addition of 1N sodium hydroxide solution. 3 g of trypsin are introduced into the solution. 1.25 kg of an insulin having 2 carboxy-terminal arginine residues results according to HPLC measurement.

After cleavage using carboxypeptidase B, human insulin results, which is additionally purified with the aid of chromatographic methods.

Human insulin corresponds to the formula I, in this formula

Y is Thr (B30);
Z is OH;
$R^1$ is Phe (B1);
$R^3$ is Asn (A21); and
A2–A20 is the amino acid sequence of the A chain of human insulin (amino acid residues 2 to 20) and B2–B29 is the amino acid sequence of the B chain of human insulin (amino acid residues 2 to 29).

Human insulin 2 consists of the SEQ ID NO:1 and SEQ ID NO:2, which are connected to one another via correctly bonded cystine bridges.

As described in EP 0 668 292, the solution is concentrated and purified by means of adsorber resin. The eluate, which contains insulin 2, can immediately be further purified on a chromatographic column after dilution with water and pH adjustment.

HPLC analysis 0.5 g of protein is dissolved for 2 min in 40 ml of a solution of 6 M guanidine hydrochloride, 50 mM tris, pH 8.5, 5 mM ethylenediamine tetraacetate (EDTA), 1% 2-mercaptoefhanol, 10 mM dithiothreitol at 95° C. and then centrifuged at 14000 g for 20 min. 0.02 ml of the clear supernatant is applied to a high-pressure liquid chromatography column.

Column: ®Nucleogel RP 300-5/46 (Macherey & Nagel, Aachen, Germany)
Gradient: Buffer A: 0.1% trifluoroacetic acid (TFA) Buffer B: 0.09% TFA in acetonitrile
Temperature: 55° C.
Total run time: 40 min
The gradient is distinguished by the following amounts of buffer B after the corresponding run times:
10 min 25%, 12 min 60%, 13 min 90%, 15 min 100%.
Flow rate: 1 ml/min
Detection: 215 nm
Retention time of insulin: approximately 19 min

EXAMPLE 2

Process According to the Present Invention

By fermentation of genetically modified *Escherichia coli* cells (EP 0 489 780), a fusion protein having the amino acid sequence shown in Example 1 is prepared (proinsulin sequence 1; SEQ ID NO:4).

The expressed fusion protein having the proinsulin sequence 1 collects in the *E. coli* cells and forms inclusion bodies. After completion of the fermentation, the cells are separated off by centrifugation and disrupted by customary high-pressure homogenization. The released fusion protein inclusion bodies are isolated by centrifugation.

5 kg of cysteine hydrochloride hydrate are added to the aqueous fusion protein suspension, which contains 40 kg of fusion protein (determined by freeze drying of an aliquot).

The suspension (the proportion of the insulin-containing fusion protein is determined with the aid of HPLC—it is 50%) having the proinsulin sequence 1 is dissolved at 40° C.

in 550 liters of an 8 M urea solution at pH 10.2. The clear solution is stirred into 9000 liters of water at a pH of 10.6 and a temperature of 15° C.

After completion of the folding reaction after about 5 hours, the content of proinsulin sequence 1 having correctly bonded cystine bridges in the reaction batch is determined with the aid of analytical HPLC as 10.0 kg, corresponding to a conversion of 50%.

The 9500 liters of solution is adjusted to a pH of 5.0 using 1N HCl and separated. A pH of 9 is then set by addition of 1N sodium hydroxide solution. 10 g of trypsin are introduced into the solution. 4 kg of an insulin having 2 carboxy-terminal arginine residues result. After cleavage using carboxypeptidase B, human insulin (SEQ ID NO:1 and SEQ ID NO:2 having correctly bonded cystine bridges) results.

The solution is concentrated and purified by means of adsorber resin. The eluate which contains human insulin can immediately be purified further on a chromatography column after dilution with water and pH adjustment.

EXAMPLE 3

Comparison Example, Prior Art

By fermentation of genetically modified *Escherichia coli* cells (EP 0 489 780), a fusion protein having the following amino acid sequence is prepared.

Proinsulin sequence 2 (SEQ ID NO:5)

```
Ala Thr Thr Ser Thr Gly Asn Ser Ala Arg Phe Val

Asn Gln His Leu Cys Gly Ser His Leu Val Glu Ala

Leu Tyr Leu Val Cys Gly Glu Arg Gly Phe Phe Tyr

Thr Pro Lys Thr Arg Arg Glu Ala Glu Asp Leu Gln

Val Gly Gln Val Glu Leu Gly Gly Gly Pro Gly Ala

Gly Ser Leu Gln Pro Leu Ala Leu Glu Gly Ser Leu

Gln Lys Arg Gly Ile Val Glu Gln Cys Cys Thr Ser

Ile Cys Ser Leu Tyr Gln Leu Glu Asn Tyr Cys Gly
```

Proinsulin sequence 2 corresponds to the formula II, in this formula

X is C-peptide of human insulin (SEQ ID NO:3);

Y is Thr (B30);

$R^1$ is Phe (B1);

$R^2$ is a peptide having 10 amino acid residues;

$R^3$ is Gly (A21); and

A2–A20 is the amino acid sequence of the A chain of human insulin (amino acid residues 2 to 20) and B2–B29 is the amino acid sequence of the B chain of human insulin (amino acid residues 2 to 29).

The expressed fusion protein having the proinsulin sequence 2 collects in the *E. coli* cells and forms inclusion bodies. After completion of the fermentation, the cells are separated off by centrifugation and disrupted by customary high-pressure homogenization. The released fusion protein inclusion bodies are isolated by centrifugation.

20 kg of the isolated fusion protein inclusion bodies (based on dry matter after freeze drying; the proportion of the insulin-containing fusion protein is determined with the aid of HPLC—it is 50%.) having the proinsulin sequence 2 are dissolved at 20° C. in 550 liters of an 8 M urea solution at pH 10.6. The clear solution is stirred into 9000 liters of an aqueous cysteine solution (5 kg of cysteine hydrochloride hydrate) at a pH of 10.6 and a temperature of 4° C.

After completion of the folding reaction after about 24 hours, the content of proinsulin sequence 2 having correctly bonded cystine bridges in the reaction batch is determined with the aid of analytical HPLC as 3.0 kg, corresponding to a conversion of 30%.

The 9500 liters of solution is adjusted to a pH of 5.0 using 1N HCl and separated. A pH of 9 is then set by addition of 1N sodium hydroxide solution. 3 g of trypsin are introduced into the solution. 0.98 kg of an insulin derivative having 2 carboxy-terminal arginine residues results according to HPLC measurement. This insulin derivative corresponds to the formula I, where Y is Thr (B30);

Z is Arg-Arg;

$R^1$ is Phe (B1);

$R^3$ is Gly (A21); and

A2–A20 is the amino acid sequence of the A chain of human insulin (amino acid residues 2 to 20) and B2–B29 is the amino acid sequence of the B chain of human insulin (amino acid residues 2 to 29), and consists of the SEQ ID NO:6 and SEQ ID NO:7, which are connected to one another via correctly bonded cystine bridges.

The solution is concentrated and purified by means of adsorber resin. The eluate which contains the insulin derivative can immediately be purified further on a chromatography column after dilution with water and pH adjustment.

EXAMPLE 4

Process According to the Present Invention

By fermentation of genetically modified *Escherichia coli* cells (EP 0 489 780), the fusion protein having the proinsulin sequence 2 (SEQ ID NO:5) is prepared according to Example 3.

The expressed fusion protein having the proinsulin sequence 2 collects in the *E. coli* cells and forms inclusion bodies. After completion of the fermentation, the cells are separated off by centrifugation and disrupted by customary high-pressure homogenization. The released fusion protein inclusion bodies are isolated by centrifugation.

5 kg of cysteine hydrochloride hydrate are added to the aqueous fusion protein suspension, which contains 40 kg of fusion protein (determined by freeze drying of an aliquot). The suspension (the proportion of the insulin-containing fusion protein is determined with the aid of HPLC—it is 50%) having the proinsulin sequence 2 is dissolved at 40° C. in 550 liters of an 8 M urea solution at pH 10.2. The clear solution is stirred into 9000 liters of water at a pH of 10.6 and a temperature of 15° C.

After completion of the folding reaction after about 5 hours, the content of proinsulin sequence 1 having correctly bonded cystine bridges in the reaction batch is determined with the aid of analytical HPLC as 10.0 kg, corresponding to a conversion of 50%.

The 9500 liters of solution is adjusted to a pH of 5.0 using 1 N HCl and separated. A pH of 9 is then set by addition of 1N sodium hydroxide solution. 10 g of trypsin are introduced into the solution. 2.8 kg of the insulin derivative result (HPLC measurement), which consists of the sequences SEQ ID NO:6 and SEQ ID NO:7, which are linked to one another via correctly bonded cystine bridges.

The solution is concentrated by means of adsorber resin and purified. The eluate which contains the insulin derivative can immediately be purified further on a chromatography column after dilution with water and pH adjustment.

What is claimed is:

1. A process for obtaining an insulin or an insulin derivative thereof having correctly bonded cystine bridges in the presence of cysteine or cysteine hydrochloride and of a chaotropic auxiliary, which comprises the following steps:

(a) mixing an aqueous suspension of a precursor of insulin or insulin derivative with an amount of cysteine or cysteine hydrochloride which results in approximately 1 to 15 SH residues of the cysteine or cysteine hydrochloride per cysteine residue of the precursor;

(b) adding the cysteine- or cysteine hydrochloride-containing suspension of the precursor into an approximately 4 to 9 molar solution of the chaotropic auxiliary at a pH of approximately 8 to 11.5 and a temperature of approximately 15° C. to 55° C., keeping the mixture obtained at this temperature for approximately 10 to 60 minutes;

(c) diluting the cysteine or the cysteine hydrochloride concentration to approximately 1 to 5 mM and diluting the chaotropic auxilary concentration to approximately 0.2 to 1.0 M in the mixture at a pH of approximately 8 to 11.5 and a temperature of approximately 5° C. to 30° C.;

(d) cleaving with trypsin or a trypsin-like enzyme-the precursor of the insulin or insulin derivative obtained by this process; and (e) purifying the insulin or insulin derivative having correctly bonded cystine bridges.

2. The process according to claim 1, wherein the chaotropic auxiliary is guanidine or guanidine hydrochloride.

3. The process according to claim 1, wherein the chaotropic auxiliary is urea.

4. The process according to claim 1, wherein the concentration of the chaotropic auxiliary in step (b) is approximately 7.0 to 9 M.

5. The process according to claim 1, wherein the temperature in step (b) is approximately 40° C.

6. The process according to claim 1, wherein the pH in step (b) is approximately 10 to 11.

7. The process according to claim 1, wherein the pH in step (c) is approximately 10 to 11.

8. The process according to claim 1, wherein in step (c) the amount of water results in a dilution of the concentration of the cysteine or of the cysteine hydrochloride in the mixture to approximately 2.5 to 3 mM, and a concentration of the chaotropic auxiliary to approximately 0.5 M.

9. The process according to claim 4, wherein the concentration of the chaotropic auxiliary in step (b) is approximately 8 M, the temperature in step (b) is approximately 40° C., the pH in step (b) is approximately 10.6, the pH in step (c) is approximately 10.6 and in step (c) the amount of water results in a dilution of the concentration of the cysteine or of the cysteine hydrochloride in the mixture to approximately 2.5 to 3 mM and a concentration of the chaotropic auxiliary of approximately 0.5 M.

10. The process according to claim 1, wherein
in step (a) the amount of cysteine or cysteine hydrochloride corresponds to an amount which results in 1 to 6 SH residues of the cysteine or cysteine hydrochloride per cysteine residue of the precursor,
in step (b) the cysteine- or cysteine hydrochloride-containing suspension of the precursor is added into an approximately 4 to 9 molar solution of the chaotropic auxiliary at a pH of approximately 8 to 11 and a temperature of approximately 30° C. to 45° C. and the mixture obtained is kept for approximately 20 to 40 minutes at this temperature; and
wherein the pH in step (c) is approximately 8 to 11 and the temperature is approximately 15° C. to 20° C.

11. The process according to claim 1, further comprising cleavage of the precursor of insulin or insulin derivative obtained in step (d) with carboxypeptidase B or a carboxypeptidase-like enzyme.

12. The process according to claim 1, wherein the insulin or insulin derivative has a formula I of

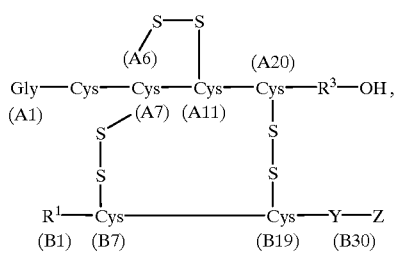

(I)

in which
Y is a genetically encodable amino acid residue;
Z is
a) an amino acid residue from the group consisting of His, Arg and Lys,
b) a peptide having 2 or 3 amino acid residues, comprising the amino acid residue Arg or Lys at the carboxyl end of the peptide,
c) a peptide having 2 to 35 genetically encodable amino acids, comprising 1 to 5 histidine residues, or
d) OH;
$R^1$ is a phenylalanine residue (Phe) or a covalent bond,
$R^3$ is a genetically encodable amino acid residue,
and wherein residues A2–A20 correspond to the amino acid sequence of the A chain of an animal insulin, or an insulin derivative thereof; and wherein residues B2–B29 correspond to the amino acid sequence of the B chain of an animal insulin or an insulin derivative thereof.

13. The process according to claim 1, wherein in step (a) the precursor of the insulin, or insulin derivative, has the formula II $$R^2—R^1—(B2–B29)—Y—X-Gly-(A2–A20)—R^3 \quad (II),$$

wherein
$R^2$ is
a) a hydrogen atom,
b) an amino acid residue from the group consisting of lysine (Lys) and arginine (Arg), or
c) a peptide having 2 to 45 amino acid residues, comprising the amino acid residue lysine (Lys) or arginine (Arg) at the carboxyl end of the peptide;
$R^1$ is a phenylalanine residue (Phe) or a covalent bond;
(B2–B29) are the amino acid residues in the positions B2 to B29 of the B chain of an animal insulin or-an insulin derivative thereof;
Y is a genetically encodable amino acid residue;
X is
a) an amino acid residue from the group consisting of lysine (Lys) and arginine (Arg), or
b) a peptide having 2 to 35 amino acid residues, comprising the amino acid residue lysine (Lys) or arginine (Arg) at the N-terminal end at the carboxyl end of the peptide, or
c) a peptide having 2 to 35 genetically encodable amino acids, comprising 1 to 5 histidine residues;
(A2–A20) are the amino acid residues in the positions A2 to A20 of the A chain of human insulin, animal insulin or an insulin derivative thereof; and
$R^3$ is a genetically encodable amino acid residue.

14. The process of claim 12, wherein the insulin or insulin derivative of formula I obtained corresponds to human insulin, wherein
Y is Thr (B30);
Z is OH;
$R^1$ is Phe (B1);
$R^3$ is Asn (A21); and
A2–A20 is the amino acid sequence of the A chain of human insulin (amino acid residues 2 to 20) and B2–B29 is the amino acid sequence of the B chain of human insulin (amino acid residues 2 to 29).

15. The process of claim 12, wherein the insulin or insulin derivative of formula I obtained corresponds to human insulin, wherein
Y is Thr (B30);
Z is Arg-Arg;
$R^1$ is Phe (B1);
$R^3$ is Gly (A21); and
A2–A20 is the amino acid sequence of the A chain of human insulin (amino acid residues 2 to 20) and B2–B29 is the amino acid sequence of the B chain of human insulin (amino acid residues 2 to 29).

16. The process according to claim 13, wherein
$R^2$ is
a) a hydrogen atom, or
b) a peptide having 2 to 25 amino acid residues, comprising the amino acid residue arginine (Arg) at the carboxyl end of the peptide;
$R^1$ is a phenylalanine residue (Phe);
(B2–B29) are the amino acid residues in the positions B2 to B29 of the B chain of human insulin;

Y is an amino acid residue from the group consisting of alanine (Ala), threonine (Thr) and serine (Ser);

X is the amino acid residue arginine (Arg) or a peptide having the amino acid sequence of the C chain of human insulin;

(A2–A20) are the amino acid residues in the positions A2 to A20 of the A chain of human insulin; and $R^3$ is an amino acid residue from the group consisting of asparagine (Asn), serine (Ser) and glycine (Gly).

17. The process according to claim 13, wherein $R^2$ is a) a hydrogen atom, or b) a peptide having 2 to 15 amino acid residues, at whose carboxyl end is found an arginine residue (Arg);

$R^1$ is a phenylalanine residue (Phe);

(B2–B29) are the amino acid residues in the positions B2 to B29 of the B chain of human insulin;

Y is a threonine residue (Thr);

X is the amino acid residue arginine (Arg) or a peptide having 2 to 35 amino acid residues, where at the beginning and at the end of the peptide there are two basic amino acid residues, in particular arginine (Arg) and/or lysine (Lys);

(A2–A20) are the amino acid residues in the positions A2 to A20 of the A chain of human insulin; and $R^3$ is the amino acid residue asparagine (Asn) or glycine (Gly).

\* \* \* \* \*

UNITED STATES PATENT AND TRADEMARK OFFICE
CERTIFICATE OF CORRECTION

PATENT NO.    : 6,380,355 B1
DATED         : April 30, 2002
INVENTOR(S)   : Franz-Josef Rubröder et al.

It is certified that error appears in the above-identified patent and that said Letters Patent is hereby corrected as shown below:

Title page,
Item [62], Related U.S. Application Data, "Aug. 19," should read -- Aug. 17, --.

Column 16,
Line 54, "auxilary" should read -- auxiliary --.
Line 58, "enzyme-the" should read -- enzyme the --.

Column 17,
Line 14, "claim 4" should read -- claim 10 --.
In the structure for formula (I), "
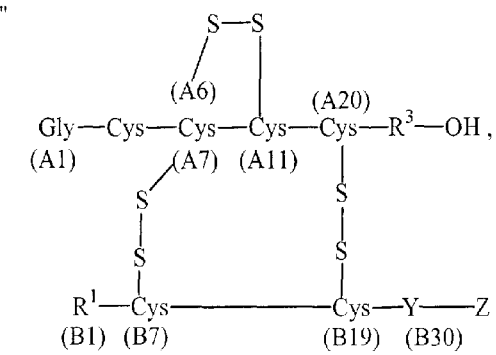
"

UNITED STATES PATENT AND TRADEMARK OFFICE
CERTIFICATE OF CORRECTION

PATENT NO. : 6,380,355 B1
DATED : April 30, 2002
INVENTOR(S) : Franz-Josef Rubröder et al.

It is certified that error appears in the above-identified patent and that said Letters Patent is hereby corrected as shown below:

should read

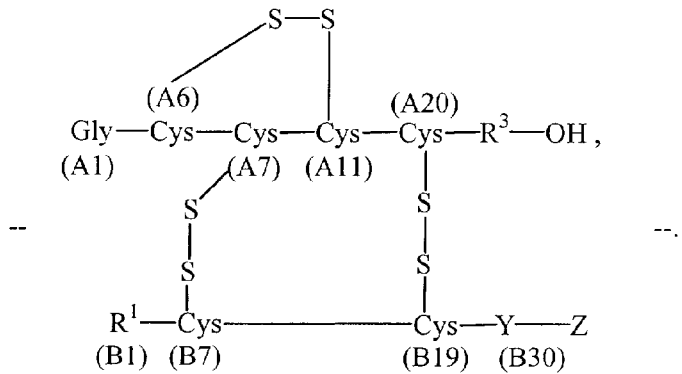

-- --.

Column 18,
Line 19, "or-an" should read -- or an --.

Signed and Sealed this

Twenty-second Day of October, 2002

Attest:

*Attesting Officer*

JAMES E. ROGAN
*Director of the United States Patent and Trademark Office*

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Escherichia coli (ix) FEATURE:
        (A) NAME/KEY: Protein
        (B) LOCATION: 1..21

(xi) SEQUENCE DESCRIPTION: SEQ ID NO: 1:

Gly Ile Val Glu Gln Cys Cys Thr Ser Ile Cys Ser Leu Tyr Gln Le
1               5                   10                  15

Glu Asn Tyr Cys Asn
            20

(2) INFORMATION FOR SEQ ID NO: 2:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Escherichia coli (ix) FEATURE:
        (A) NAME/KEY: Protein
        (B) LOCATION: 1..30

(xi) SEQUENCE DESCRIPTION: SEQ ID NO: 2:

Phe Val Asn Gln His Leu Cys Gly Ser His Leu Val Glu Ala Leu Ty
1               5                   10                  15

Leu Val Cys Gly Glu Arg Gly Phe Phe Tyr Thr Pro Lys Thr
            20                  25                  30

(2) INFORMATION FOR SEQ ID NO: 3:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Escherichia coli (ix) FEATURE:
        (A) NAME/KEY: Protein
        (B) LOCATION: 1..35

(xi) SEQUENCE DESCRIPTION: SEQ ID NO: 3:

```
Arg Arg Glu Ala Glu Asp Leu Gln Val Gly Gln Val Glu Leu Gly Gl
1               5                   10                  15

Gly Pro Gly Ala Gly Ser Leu Gln Pro Leu Ala Leu Glu Gly Ser Le
            20                  25                  30

Gln Lys Arg
        35
```

(2) INFORMATION FOR SEQ ID NO: 4:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Escherichia coli (ix) FEATURE:
        (A) NAME/KEY: Protein
        (B) LOCATION: 1..96

(xi) SEQUENCE DESCRIPTION: SEQ ID NO: 4:

```
Ala Thr Thr Ser Thr Gly Asn Ser Ala Arg Phe Val Asn Gln His Le
1               5                   10                  15

Cys Gly Ser His Leu Val Glu Ala Leu Tyr Leu Val Cys Gly Glu Ar
            20                  25                  30

Gly Phe Phe Tyr Thr Pro Lys Thr Arg Arg Glu Ala Glu Asp Leu Gl
            35                  40                  45

Val Gly Gln Val Glu Leu Gly Gly Pro Gly Ala Gly Ser Leu Gl
50                  55                  60

Pro Leu Ala Leu Glu Gly Ser Leu Gln Lys Arg Gly Ile Val Glu Gl
65                  70                  75                  80

Cys Cys Thr Ser Ile Cys Ser Leu Tyr Gln Leu Glu Asn Tyr Cys As
                85                  90                  95
```

(2) INFORMATION FOR SEQ ID NO: 5:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Escherichia coli (ix) FEATURE:
        (A) NAME/KEY: Protein
        (B) LOCATION: 1..96

(xi) SEQUENCE DESCRIPTION: SEQ ID NO: 5:

```
Ala Thr Thr Ser Thr Gly Asn Ser Ala Arg Phe Val Asn Gln His Le
1               5                   10                  15

Cys Gly Ser His Leu Val Glu Ala Leu Tyr Leu Val Cys Gly Glu Ar
            20                  25                  30

Gly Phe Phe Tyr Thr Pro Lys Thr Arg Arg Glu Ala Glu Asp Leu Gl
            35                  40                  45

Val Gly Gln Val Glu Leu Gly Gly Pro Gly Ala Gly Ser Leu Gl
50                  55                  60
```

-continued

```
Pro Leu Ala Leu Glu Gly Ser Leu Gln Lys Arg Gly Ile Val Glu Gl
65                  70                  75                  80

Cys Cys Thr Ser Ile Cys Ser Leu Tyr Gln Leu Glu Asn Tyr Cys Gl
                85                  90                  95
```

(2) INFORMATION FOR SEQ ID NO: 6:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Escherichia coli (ix) FEATURE:
        (A) NAME/KEY: Protein
        (B) LOCATION: 1..32

(xi) SEQUENCE DESCRIPTION: SEQ ID NO: 6:

```
Phe Val Asn Gln His Leu Cys Gly Ser His Leu Val Glu Ala Leu Ty
1               5                   10                  15

Leu Val Cys Gly Glu Arg Gly Phe Phe Tyr Thr Pro Lys Thr Arg Ar
                20                  25                  30
```

(2) INFORMATION FOR SEQ ID NO: 7:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Escherichia coli (ix) FEATURE:
        (A) NAME/KEY: Protein
        (B) LOCATION: 1..21

(xi) SEQUENCE DESCRIPTION: SEQ ID NO: 7:

```
Gly Ile Val Glu Gln Cys Cys Thr Ser Ile Cys Ser Leu Tyr Gln Le
1               5                   10                  15

Glu Asn Tyr Cys Gly
                20
```